(12) United States Patent
Kong et al.

(10) Patent No.: US 11,959,093 B2
(45) Date of Patent: Apr. 16, 2024

(54) INTEGRATION SITES AND USES THEREOF

(71) Applicant: APPLIED STEMCELL, INC., Milpitas, CA (US)

(72) Inventors: Ling-Jie Kong, Union City, CA (US); Ruby Yanru Tsai, San Jose, CA (US); Xiuling Chi, San Jose, CA (US)

(73) Assignee: APPLIED STEMCELL, INC., Milpitas, CA (US)

( * ) Notice: Subject to any disclaimer, the term of this patent is extended or adjusted under 35 U.S.C. 154(b) by 0 days.

(21) Appl. No.: 16/492,950

(22) PCT Filed: Mar. 14, 2018

(86) PCT No.: PCT/US2018/022274
§ 371 (c)(1),
(2) Date: Sep. 11, 2019

(87) PCT Pub. No.: WO2018/175153
PCT Pub. Date: Sep. 27, 2018

(65) Prior Publication Data
US 2020/0017884 A1    Jan. 16, 2020

Related U.S. Application Data

(60) Provisional application No. 62/473,454, filed on Mar. 19, 2017.

(51) Int. Cl.
| | |
|---|---|
| *C12N 15/79* | (2006.01) |
| *C07H 21/04* | (2006.01) |
| *C12N 15/113* | (2010.01) |
| *C12N 15/90* | (2006.01) |
| *C07H 21/02* | (2006.01) |
| *C12N 15/63* | (2006.01) |
| *C12N 15/85* | (2006.01) |
| *C12N 15/86* | (2006.01) |

(52) U.S. Cl.
CPC .......... *C12N 15/907* (2013.01); *C12N 15/113* (2013.01); *C07H 21/02* (2013.01); *C07H 21/04* (2013.01); *C12N 15/63* (2013.01); *C12N 15/79* (2013.01); *C12N 15/85* (2013.01); *C12N 15/86* (2013.01); *C12N 2310/20* (2017.05)

(58) Field of Classification Search
CPC ........ C12N 15/63; C12N 15/79; C12N 15/85; C12N 15/86; C12N 15/907; C12N 2310/20; C07H 21/02; C07H 21/04
See application file for complete search history.

(56) References Cited

U.S. PATENT DOCUMENTS

| | | |
|---|---|---|
| 2006/0223772 A1 | 10/2006 | Williams et al. |
| 2009/0221437 A1 | 9/2009 | Harkin et al. |
| 2010/0112640 A1 | 5/2010 | Antoniou et al. |
| 2015/0140665 A1 | 5/2015 | Calos et al. |
| 2016/0115502 A1 | 4/2016 | Shen et al. |

FOREIGN PATENT DOCUMENTS

WO    00/05393 A2    2/2000

OTHER PUBLICATIONS

Florin et al., 2012, US 20120190065 A1.*
Kotterman et al., 2014, Nature Reviews, vol. 15, p. 445-451.*
Shim et al., 2017, Current Gene Therapy, vol. 17, No. 5, p. 1-18.*
Lenzi et al., 2014, NCBI Bookshelf, a Service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16.*
Williams et al., 2008, US 20080222742 A1.*
Bahr, et al., 2016, US 20160145645 A1.*
Khodarovich et al., 2013, Applied Biochemistry and Microbiology, vol. 49, No. 9, pp. 711-722.*
Selsby et al., 2015, ILAR Journal, vol. 56, No. 1, p. 116-126.*
Maksimenko et al., 2013, Acta Naturae, vol. 5, No. 1, p. 33-46.*
Yang et al., 2016, PNAS, 113(41), E6209-E6218, p. 1-10.*
Kozu et al., 2002 (GenEmbl Accession No. D28877, computer printout, pp. 1-7).*
Al-Lazikani, B. et al., "Standard conformations for the canonical structures of immunoglobulins", Journal of Molecular Biology (1997), vol. 273, pp. 927-948.
Chothia, C. et al., "Domain association in immunoglobulin molecules", Journal of Molecular Biology (1985), vol. 186, pp. 651-663.
Chothia, C. et al., "Canonical structures for the hypervariable regions of immunoglobulins", Journal of Molecular Biology (1987), vol. 196, pp. 901-917.
Chothia, C. et al., "Conformations of immunoglobulin hypervariable regions", Nature (1989), vol. 342, pp. 877-883.
Gardiner-Garden, M. et al., "CpG Islands in vertebrate genomes", Journal of Molecular Biology (1987), vol. 196, pp. 261-282.
Rice, P. et al., "EMBOSS: The European Molecular Biology Open Software Suite", Trends in Genetics (2000), vol. 16, pp. 276-277.
Bird, A. et al., "A fraction of the mouse genome that is derived from islands of nonmethylated, CpG-rich DNA", Cell (1985), vol. 40, pp. 91-99.
Tazi, J. et al., "Alternative chromatin structure at CpG islands", Cell (1990), vol. 60, pp. 909-920.
Wise, T. L. et al., "The Undermethylated State of a CpG Island Region in Igf2 Transgenes Is Dependent on the H19 Enhancer", Genomics (1999), vol. 60, pp. 258-271.

(Continued)

*Primary Examiner* — Shin Lin Chen
(74) *Attorney, Agent, or Firm* — Jun He Law Offices P.C; James J. Zhu

(57) ABSTRACT

The present disclosure provides compositions and methods for enhanced expression of exogenous genes in eukaryotic cells. The method involves introducing into a mammalian cell an exogenous nucleic acid. wherein the exogenous nucleic acid intearates into a locus of the genome that comprises an extended methylation-free CpG island. Also provided are chromosomal loci, sequences for enhanced and stable expression of exogenous genes.

10 Claims, 2 Drawing Sheets
Specification includes a Sequence Listing.

(56) References Cited

OTHER PUBLICATIONS

Antequera, F. et al., "Number of CpG islands and genes in human and mouse", Proceedings of the National Academy of Sciences (1993), vol. 90, pp. 11995-11999.
Cross, S. H. et al., "CpG islands and genes", Current Opinion in Genetics & Development (1995), vol. 5, pp. 309-314.
Grindley, N. D. F. et al., "Mechanisms of Site-Specific Recombination", Annual Review of Biochemistry (2006), vol. 75, pp. 567-605.
Esposito, D. et al., "The integrase family of tyrosine recombinases: evolution of a conserved active site domain", Nucleic Acids Research (1997), vol. 25, pp. 3605-3614.
Nunes-Duby, S. E. et al., "Similarities and differences among 105 members of the Int family of site-specific recombinases", Nucleic Acids Research (1998), vol. 26, pp. 391-406.
Marshall Stark, W. et al., "Catalysis by site-specific recombinases", Trends in Genetics (1992), vol. 8, pp. 432-439.
Keown, W. A. et al., "Methods for introducing DNA into mammalian cells", Methods in Enzymology (1990), vol. 185, pp. 527-537.
International Search Report of PCT Application No. PCT/CN2018/022274, dated Jun. 7, 2018.
Xiaoxiao Zhu et al: "An Efficient Genotyping Method for Genome-modified Animals and Human Cells Generated with CRISPR/Cas9 System", Scientific Reports, vol. 4, No. 1, Sep. 19, 2014 (Sep. 19, 2014), XP055461892, DOI: 10.1038/srep06420. abstract; p. 5, right-hand column, paragraph 2; p. 7; figures 7C, 7D.
Antoniou M et al: "Transgenes encompassing dual-promoter CpG islands from the human TBP and HNRPA2B1 loci are resistant to heterochromatin-mediated silencing", Genomics, Academic Press, San Diego, US, vol. 82, No. 3, Sep. 1, 2003 (Sep. 1, 2003), pp. 269-279, XP004442995, ISSN: 0888-7543, DOI: 10.1016/S0888-7543(03)00107-1. abstract; p. 273; figures 3,4.
Katsantoni Eleni Z et al: "Ubiquitous expression of the rtTA2S-M2 inducible system in transgenic mice driven by the human hnRNPA2BI/CBX3 CpG island", BMC Developmental Biology, Biomed Central Ltd., London, GB, vol. 7, No. 1, Sep. 27, 2007 (Sep. 2007), p. 108, XP021032179, ISSN: 1471-213X. abstract; p. 2, right-hand column, paragraph 2; p. 3; figure 1.
The extended European search report of European application No. 18772375.4, dated Dec. 14, 2020.
Steven Williams et al., "CpG-island fragments from the HNRPA2B1/CBX3 genomic locus reduce silencing and enhance transgene expression from the hCMV promoter/enhancer in mammalian cells", BMC Biotechnology, vol. 5, No. 17, pp. 1-9, Jun. 3, 2005.
Second Office Action of the corresponding Chinese application No. 201880018555.5, dated Jun. 1, 2023.

* cited by examiner

SEQUENCE LISTING

```
<160> NUMBER OF SEQ ID NOS: 7

<210> SEQ ID NO 1
<211> LENGTH: 4000
<212> TYPE: DNA
<213> ORGANISM: Cricetulus griseus

<400> SEQUENCE: 1
ccgggaaccg gatttggcgg ccgccatttt cccgtctcct tgctcgcagc ggttttttcgc      60 gtcccgcact ctgcggctct gcccgttcgg cccctteccc cccgcgtggg agccattagc     120
```

```
tggtttcctt tgtccccggc ccgttttggt ggcgttccga gggggatctg gggtgttttg      180
agctctgatc tcggagtcct gcgcacctcg ttttaggcgc tccgccctcc ttcccctcg       240 acgaaatggc gccattgcgc tcccgagcca cacggtgtgc gcggccgggt ggggtggcg       300 gcggcctccg caagggttcc cggcgcaggc cccgggcgag gagtgcgatc cgggcctgag      360
cctgctgctg aaggcagcct tgcagcaaag aaaccatttt acttccccga gctggctcct      420 aattcctttta attaagcgat tgtgagtct gcagttgtaa aaggaagccc agagtgctca      480
gctgtagtta aaggtgatc ttgggcggag ggatatttttt ttattgctgc gtatgtttat     540
tttcctgaag atcctgatg tttgaaataa ttcagattat gaggatttta aagggaacca       600
caggatttgt tcctaaaaca acagatcttt acgcgtgatg gtcacgttag ggaagagaaa      660
ataacttttc gtagttcacc tttgattaca gcatggaaca gtccagtatt aacgcaggaa      720
cctagctatg taaaaacttt tatttgggac acaatgtatt tgaactttgt catttgcttt     780
tttctgattt atgtttgcaa atggttgatt attacattga taagcataag gtttcaaatt      840 aaagggggtct acttggttat attctttgac cctaagcacg tttataaaat aaccttgttt     900
ataatcgata gtggacgtcg ggtaagtttg gaaaaaccta tgaggtaagt aataagcttt     960
tgctttttgt tagtgacatt aaaaatggta agtttatgct tacagtttga atttaaagat     1020
ggcacatctg tggacattta tctagaattg cctggaaact tggatttcca gtcatactaa     1080
gtattttaca cgtcctattt taatctttaa cctatttgt ctactcaatt tctccaaatt      1140
tcagaacctg agaaagggca tcgaacaaaa ttttttacaga cttttttttga aggaaccttta  1200 atagatttgg gttgtaataa gagttgtgga aattttttgt gtgttatgaa ttttgtcttt     1260
tcagtttgtt atgcaatcaa gacaggtcct ggatagtatt acccagttta taagcatctt     1320 ggttttttaag ctgttttatt tataagtcag taataacaca actttagtat ttacttcagg    1380
aaattactat tggaaatttt tgagagattt gtcagaaggc cactaattac taaaaggaaa     1440
gttaagccag gcgttggtgg cgcacgcctt taatcccaga ggcaggcgga tatttgtgag     1500
ttcgaggcca gcctggtctc cagagcgagt gccaggatag gctccaaaaa aaatgtaaag     1560
taactgttgg ggcaatagca actgtagata aatgtgtgct tcttagtact gtagcctgaa     1620
caccagacaa ggagtgcctc ccaaaaaatt agatggaata aattttgcta agttaaaaga    1680
aaactatttt gaggtggtgc gtatatctgg tgttcaactt tactcatgga acttcttttca   1740 gagttgaagg atcccccatt gaaatagtta gtctaactcc agggtggggg ggcagtttaa    1800
ggaaaggcag atctgccact actctgaaat tgaatcctga attaagcagt ggatatcgaa    1860
atttcagggt ttttttttttt caatttaaaa aaataagttt gagcaaagtt ctgtgcttga   1920
gttgtagact ttaataaaga atttcataag aattctttga tacccttttaa atcagagttg   1980 gttatggttt ttctcaaagg ttttttaagaa agtgtaagct aaggtaattt atatgaatta   2040
aagttagatc aaatattagt gactttaaaa cttgcatagt tcagctgagg caattttttgg   2100 tgtaacacaa ctaatatgca gtttaacata tggtttaaat ttgatgtaag tttttttttt    2160 cccccccagaa aactttagaa actgttcctt tggagaggaa aaaggtactc tgccagcagg    2220
tcacctcata tttaagaatt taatttcctg catacaaaga gaaaatgtaa ataaaaattg     2280
aaatggtatt ttcctttaca gagagaaaag gagcagttcc gcaaactctt tattggtggc    2340
ttaagctttg aaactacaga agaaagtttg agaaactact atgagcaatg gggaaagctc    2400
acagactgtg tggtacgtta aatgtgaaag tctgactgtg ggttttagta tggttgagtt    2460
```

| | |
|---|---|
| taagcataaa ttttgggctg agccagcctg cagtgccaca tgcctttagt cccagccctt | 2520 |
| agagtctggc ggatctctga gtttgagacc agactggtct ataagagcta gttccaggac | 2580 |
| agcctccaaa gacacagaga agccctgtc tcccaaaaat ccaaaaagga taattttctt | 2640 |
| gttgggatga atcatacagg aaattagtat ataaaaaagg acattgggc gggctctcaa | 2700 |
| acagggtgtc tctgtaacca accacattag cctcgaactc ttctctccaa attctgagat | 2760 |
| taaaggcgtg tgctaccaca cctggccaaa aaaaaaaaa aataaaaaa gaccaattgg | 2820 |
| tttgttcata actaccttga aattaatgct gacatctttt ggttttaaag gttatgagag | 2880 |
| atcctgcaag caaagatca aggggatttg gatttgtaac attctcatcc atggctgagg | 2940 |
| tagatgctgc catggctgca aggcctcatt ccattgatgg cagagtagtt gagccaaaac | 3000 |
| gtgctgtagc aagagaggtg agcaaaatat gttcagtggt tttcttgggt tgtactagct | 3060 |
| ttttgtacat gactttctag gacttaactt caaatctatt gctatatctg aaggaatttg | 3120 |
| tcctaagact gaagtataag tttgtgcttt caaggtggtt taatttgtgt atttgttttt | 3180 |
| tctgtcagat aactttgtca ctatctgttg taggagtctg gaaaaccagg agcccatgtg | 3240 |
| actgtgaaga aactgtttgt cggtggaatt aaagaggata ctgaggaaca ccaccttaga | 3300 |
| gattactttg aagaatatgg gaaaattgat actattgaaa taattactga taggcagtct | 3360 |
| gggaagaaaa gaggctttgg ctttgttact tttgatgacc atgatcctgt ggataaaatt | 3420 |
| gtatgtaagt gtctaggcat aagagtggtt gtatataaaa tgttgggtgt attaacagcc | 3480 |
| tgttaaaaca ttcaggattg cactgggtgt tggtggcaca cacctttaat cccagcactc | 3540 |
| aggaggcaga ggcaggcgga tatgtgtgag ttccaggcca acctggtctc tagagccagt | 3600 |
| gccaggatag gctccaaagc tacacagaga aaccctgtct ggaaaaacca aagaaaaat | 3660 |
| tgcttattag aatgtattta tgattcagtt ttttgtttt tgtttcagtg caaaaatatc | 3720 |
| acaccatcaa tggtcacaat gcagaagtta gaaaggcatt gtctagacaa gaaatgcaag | 3780 |
| aagtccaaag ttctaggagt ggacgaggag gtaagaaatc atacattttt agatttgtgt | 3840 |
| attttatatg tatatataca tttgatgggt tttgtctgaa tgcttgctac taatcaaaac | 3900 |
| atatatccta ggaaactttg gttttggtga ttctcgtggt ggcggcggca attttggacc | 3960 |
| aggaccagga agcaacttca ggggggttc tggtgagtgt | 4000 |

<210> SEQ ID NO 2
<211> LENGTH: 4000
<212> TYPE: DNA
<213> ORGANISM: Homo sapiens

<400> SEQUENCE: 2

| | |
|---|---|
| taattaaata acaaaaggaa aaaacttaag atgcttcaac cccgtttcgt gacactttga | 60 |
| aaaagaatc acctcttgca aacacccgct cccgacccc gccgctgaag cccggcgtcc | 120 |
| agaggcctaa gcgcgggtgc ccgccccac ccgggagcgc gggcctcgtg gtcagcgcat | 180 |
| ccgcggggag aaacaaaggc cgcggcacgg gggctcaagg gcactgcgcc acaccgcacg | 240 |
| cgcctacccc cgcggcggcc acgttaactg ggcggtcgcc gcagcctcgg gacagccggc | 300 |
| cgcgcgccgc caggcctcgc ggacgcggga ccacgcgccg cctccggga gcccaagtc | 360 |
| tcgacccagc ccgcgtggc ggctgggga gggggcgcct ccgccggaac gcgggtgggg | 420 |
| gaggggaggg ggaaatgcgc tttgtctcga aatggggcaa ccgtcgccac agctccctac | 480 |
| cccctcgagg gcagagcagt cccccacta actaccggcg ctggccgcgc gccaggccag | 540 |
| ccgcgaggcc accgcccgac cctccactcc ttcccgcagc tcccggcgcg gggtccggcg | 600 |

```
agaagggggag gggagggggag cggagaaccg ggccccccggg acgcgtgtgg catctgaagc      660
accaccagcg agcgagagct agagagaagg aaagccaccg acttcaccgc ctccgagctg      720
ctccgggtcg cgggtctgca gcgtctccgg ccctccgcgc ctacagctca agccacatcc      780 gaaggggggag ggagccggga gctgcgcgcg gggccgccgg ggggaggggt ggcaccgccc     840
acgccgggcg gccacgaagg gcggggcagc gggcgcgcgc ccggcggggg gaggggccgc      900
gcgccgcgcc cgctgggaat tggggcccta gggggagggc ggaggcgccg acgaccgcgg      960
cacttaccgt tcgcggcgtg gcgcccggtg gtccccaagg ggagggaagg gggaggcggg     1020
gcgaggacag tgaccggagt ctcctcagcg gtggcttttc tgcttggcag cctcagcggc      1080
tggcgccaaa accggactcc gcccacttcc tcgcccctgc ggtgcgaggg tgtggaatcc      1140
tccagacgct gggggagggg gagttgggag cttaaaaact agtacccctt tgggaccact      1200
ttcagcagcg aactctcctg tacaccaggg gtcagttcca cagacgcggg ccaggggtgg      1260
gtcattgcgg cgtgaacaat aatttgacta gaagttgatt cgggtgtttc cggaaggggc      1320
cgagtcaatc cgccgagttg gggcacggaa acaaaaagg gaaggctact aagattttc      1380 tggcgggggt tatcattggc gtaactgcag ggaccacctc ccgggttgag ggggctggat      1440
ctccaggctg cggattaagc ccctcccgtc ggcgttaatt tcaaactgcg cgaccgtttc      1500
tcacctgcct tgcgccaagg caggggggcgg gaccctattc caagaggtag taactagcag      1560
gactctagcc ttccgcaatt cattgagcgc atttacggaa gtaacgtcgg gtactgtctc      1620
tggccgcaag ggtgggagga gtacgcattt ggcgtaaggt ggggcgtaga gccttcccgc      1680
cattggcggc ggatagggcg tttacgcgac ggcctgacgt agcggaagac gcgttagtgg      1740
gggggaaggt tctagaaaag cggcggcagc ggctctagcg gcagtagcag cagcgccggg      1800
tcccgtgcgg aggtgctcct cgcagagttg tttctcgagc agcggcagtt ctcactacag      1860
cgccaggacg agtccggttc gtgttcgtcc gcggagatct ctctcatctc gctcggctgc      1920
gggaaatcgg gctgaagcga ctgagtccgc gatggaggta acgggtttga aatcaatgag      1980
ttattgaaaa gggcatgcg aggccgttgg cgccctcagtg gaagtcggcc agccgcctcc      2040
gtgggagaga ggcaggaaat cggaccaatt cagtagcagt ggggcttaag gtttatgaac      2100
ggggtcttga gcggaggcct gagcgtacaa acagcttccc caccctcagc ctccccggcgc      2160 catttcccctt cactggggt ggggatggg gagctttcac atggcggacg ctgccccgct      2220
ggggtgaaag tggggcgcgg aggcgggaat tcttattccc tttctaaagc acgctgcttc      2280
gggggccacg gcgtctcctc ggcgagcgtt tcggcgggca gcaggtcctc gtgagcgagg      2340
ctgcggagct tccccctccccc ctctctcccg ggaaccggat ttggcggccg ccatttttcat      2400 ggctcgcctt cctctcagcg ttttcctat aactcttta ttttcttagt gtgctttctc      2460
tatcaagaag tagaagtggt taactatttt ttttcttct cgggctgttt tcatatcgtt      2520
tcgaggtgga tttggagtgt tttgtgagct tggatcttta gagtcctgcg cacctcatta      2580
aaggcgctca gccttcccct cgatgaaatg gcgccattgc gttcggaagc cacaccgaag      2640
agcggggagg gggggtgctc cgggtttgcg ggcccggttt cagagaagat atcaccaccc      2700
agggcgtcgg gccgggttca atgcgagccg taggacaaag aaaccatttt atgttttttcc      2760 tgtcttttttt ttccttttgag taacggtttt atctgggtct gcagtcagta aaacgacaga      2820
tgaaccgcgc caaaataaac ataaaattgga agccatcggc cacgaggggc agggacgaag      2880
gtggttttct gggcgggggga gggatattcg cgtcagaatc ctttactgtt cttaaggatt      2940
```

| | |
|---|---|
| ccgtttaagt tgtagagctg actcatttta agtaatgttg ttactgagaa gtttaaccct | 3000 |
| tacgggacag atccatggac ctttatagat gattacgagg aaagtgaaat aacgattttg | 3060 |
| tccttagtta tacttcgatt aaaacatggc ttcagaggct ccttcctgta atgcgtatgg | 3120 |
| attgatgtgc aaaactgttt tgggcctggg ccgctctgta tttgaacttt gttactttc | 3180 |
| tcattttgtt tgcaatcttg gttgaacatt acattgataa gcataaggtc tcaagcgaag | 3240 |
| ggggtctacc tggttatttt cttgacccct aagcacgttt ataaaataac attgtttaaa | 3300 |
| atcgatagtg gacatcgggt aagtttggat aaattgtgag gtaagtaatg agttttgct | 3360 |
| ttttgttagt gatttgtaaa acttgttata aatgtacatt atccgtaatt tcagtttaga | 3420 |
| gataacctat gtgctgacga caattaagaa taaaaactag ctgaaaaaat gaaaataact | 3480 |
| atcgtgacaa gtaaccattt caaaagactg ctttgtgtct cataggagct agtttgatca | 3540 |
| tttcagttaa ttttttcttt aattttacg agtcatgaaa actacaggaa aaaaatctga | 3600 |
| actgggtttt accactactt tttaggagtt gggagcatgc gaatggaggg agagctccgt | 3660 |
| agaactggga tgagagcagc aattaatgct gcttgctagg aacaaaaaat aattgattga | 3720 |
| aaattacgtg tgactttta gtttgcatta tgcgtttgta gcagttggtc ctggatatca | 3780 |
| ctttctctcg tttgaggttt tttaacctag ttaacttta agacaggttt ccttaacatt | 3840 |
| cataagtgcc cagaatacag ctgtgtagta cagcatataa agatttcagc tctgaggttt | 3900 |
| ttcctattga cttggaaaat tgttttgtgc ctgtcgcttg ccacatggcc aatcaagtaa | 3960 |
| gcttcagctt tcagtaattg ttatcttaga gattatgcca | 4000 |

<210> SEQ ID NO 3
<211> LENGTH: 4000
<212> TYPE: DNA
<213> ORGANISM: Mus musculus

<400> SEQUENCE: 3

| | |
|---|---|
| aggattgtta ctttcccaat ccatatagaa ttttaacaat tttagtgttt attttggatg | 60 |
| aaaggaaatg actatctttt gttagcaaat taccataaga tcttttctt tagatttctg | 120 |
| aatactccaa ggagctcata taattccatc cttattttt cagaggccct ccctgttcaa | 180 |
| tcacggtata aaaaaggaa cacattaaga tgtcccagtc ctattttctg gcttttttt | 240 |
| tccgggggtg gtggtgcggt aatcactctc tatagtccag tctgggcttc aacgcctggc | 300 |
| aatccccagc ctcaagctcc caagtactgt cctgataagg atagaaggag tcgacctcct | 360 |
| tcacgctccc ctccgaggag ggctccttcc cagctccatt ccccggtcgg agcccgtcc | 420 |
| cccacccgag agcgcgggcc tcgtggtcag cgcctccgcg gggagaaaca aaggcggcgg | 480 |
| cgggggctca agggcactgc gccacggggcc cgcgcctccc ccatccggcg gcggccacgt | 540 |
| agccgggagc gcgccgcagc ccggagcctc gggcctcgca gctgcagagc ctgaaccgct | 600 |
| ctctccctgc gggcctgcga cgaggctggg ggaggggagg cccgcgcttt gtctggagtc | 660 |
| tcggtagctg tcatccggct cccacccctca tgcacaattg tcccatctcc cccacgcacc | 720 |
| ggcgcggcgc ccgcctcagc gaggcccag ccggtttccc gcagcccgcg gcccacgggg | 780 |
| ctcgcagcct ccccgcaagc tcggacgcac ggagcatccc aaaccccacc acacgcaaga | 840 |
| tcgaaaaaaa gcaaaggcac gaacttcacc gctccgatgc tcagggccgc ggatcctgca | 900 |
| gagtctcccg cctgcgcgct tcggttcagc cacatccgag ggggagggggc gcgggcagct | 960 |
| ccgccggggg ggaggggggag caccgcccac gccctggccg cgcggggccc gccgggaacg | 1020 |
| cgtcctgcgg ggggcggcgc gcgcaatgct caccgtccgc ggcgtggcgc ccaggggggtc | 1080 |

-continued

```
tcctggctgg ggggagggg gggaaggcgg gcaggaagga ccgcggaggc ctctctgcgt    1140
ctcggagcgc gccaaagcgg ggctccaccc acctccttgc ccggatcttg aaggccgggg    1200
agataaacag cggggttctt taagcaccac ctctcactag gcgcgggatc ccaaggcttg    1260
tggcatccgg ggtggtactt ggactaaaag tccttctggg agggaccgag tgagaacccc    1320
tttgggacgt gtagaaatat ttgtgtggtt cgagaatatt tgtgcggacg ggcttggcaa    1380
aggcgtagct gcagagagca cgcttgggtg gagagggccg cacgcccag cgccggccta    1440 agcccctccc gacggcgtta tttcaaactg cgcgaccgtt tctccgctcc ctacgcggag    1500
gtgggggccg gacctagttc cggacgtagt aacacgccga gcgcgagcct tccgcaattc    1560
acggaacaca gttgcgcaag tgatgtaaag cagtcccgct gtacctaaag ggggagtgtc    1620
acgtacttgg cgtaaggaga gtgtaggccc ttccgccat tggcggcggt tagggcgttt    1680
acgtaacggc gtgacgtaag cggagacgcg ttagtggggg gaaggttcta gaaaagcggc    1740
ggtctcggct ccagcggcag tagcagcggc gccggtcccg tgtgcaggag ctcctttgcg    1800
gcccagtttc ttggccatcg cctgctctcc ccacagcgcc aggacgagtc ccgtgcgcgt    1860
ccgtccgcgg aggtctttct catctcgctc ggctgcggga atcgggctg aagcgactga    1920 gtccgcgatg gaggtaacgg gttgaaatc aatgagttat taaaaatggc atggcgaggc    1980
cgtaggcacc gcaatggaaa ccggccaccc gcctccgtgg tccggcggag gggatgcggc    2040
cactcgagtg gcggttggcc ttggcgagtt tctgaggggt cgttggagga ggcctctgat    2100
tgtccgaccg ccttccccgc cctcagccgc ccggcgccat ttccctcagt tggggtgggg    2160
gatgggaagt gcccgccgcg accgggctgg accgctaaag tagcgcgtga gcgggccatc    2220
gctggccttt cgatgtgcgc gggcctaggg gctcggttgt gttcgcggcg aacgtttct    2280 ggggcccccc cggcttcccg gagcgagtct gcgaagcttc ccctcccccc tctcccggga    2340
accggatttg gcggccgcca tttttcccgtc tccttcctcg ccacgatttt gctttcaacg    2400
ctttaggttt actagtttgg ttttcttttt tcaccactgc gtagacgtgt ttagcgattt    2460
tcctttcttt tggaagtctt cataccgttt cgaggtggat ttagcgtttt gagcttgggt    2520
cttcagcgtc ctgcgcacct cgctaaaggc tctctgcctt cccctcgacg aaatggcgcc    2580
attgctttct gaagccaccg aggcgcgggg tgggggcggg gtggcggcgc tccacgagct    2640
ttactggaac aggcagagag aacgtagtac aaccgaggcc tgggcgggtg gctgaaggca    2700
gcgtcgctgc aaagagaccg ttttattttt cataatacgt aagattacgg gtgctgtagt    2760
aaagcacttg agcattagta tagtaggagg aagtcaaagt ggaaaaaatg ggagcgctca    2820
tcaggaagct agggaggcta tgttgagtgc agggttactt tccttttatt gcagaacttt    2880
tatctgctta aaggatcctc ggatcgaaat aattcaaatt ataagcattt ttaagggaat    2940
cttcgaattt gttggtaaag tcaacggatc cttagcacgt ggtgttcact ttaaggaagt    3000
gaaatagctg acttttcata gttagccttc gcttaaagcc tggttcagtg gacgaaaatc    3060
cacgtcctgg ctatataaaa acttagtttg gggtcacagt gtttgagcgt ggtcattcgg    3120 ttttttttatt ttttatttgt ttgaaattat gatgcatcat tacactgata agcattagct    3180
ttcgaattga aaggggtctc cttggttatt ttctttgact ctaagcacac ttataaataa    3240
aataaccttg tttataatcg atagtggacg tctggtaagt ttggaaaaaa cccgaggtaa    3300
gtaaagagct tttgctttcg ttagtgatat gaaaaaacaa ggtgtattta atacttgcaa    3360
cttagtttaa ggaaagccaa tttactgaca ttttagtaga gctaccagaa acactatttg    3420
```

-continued

```
gagtcctgat taaggctttt gtaactattt tgactatta aaacaattt ggtcgttttt    3480 attaaacatt tcaaaaccta aaaattgtaa acattggctt tttgagcaca ttttggagaa    3540
acttacaaat ttaggctata cagtaaaata acggatttgt tttataattt tgcttttca    3600 tttcgttgtg cagtcatagg tcctggatag tatgacctaa tttatgaaca tcttgataag    3660
tttttgtact tagctattgg aaagccagta ttaagtgcct gacaaaacca gatttaaggt    3720
gatatctgga gtttcagcat tcttcatgga gcttgtttca gagttgcagg atttttttt    3780 ttcatcttga gatacttaca attaacacca gaggggcag ctcagggaaa agcaaatatg    3840 ccactttca gaaactgaat cttggaagtg gtgaatttgg aaacaggttt tttaaatttt    3900
ttttaaatct aaaaagtagt aaattttgga cttgggttgt agaatttaat gaattacaaa    3960
agaattcttt aatacccttt aaatgaccta agagctgggt                         4000
```

<210> SEQ ID NO 4
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(21)
<223> OTHER INFORMATION: n is a, c, g, or t

<400> SEQUENCE: 4
tgtaaaatac ttagtatgac ngg                                           23

<210> SEQ ID NO 5
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(21)
<223> OTHER INFORMATION: n is a, c, g, or t

<400> SEQUENCE: 5
tgacaatggg accagtagta ngg                                           23

<210> SEQ ID NO 6
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(21)
<223> OTHER INFORMATION: n is a, c, g, or t

<400> SEQUENCE: 6
actctgatca gctatcttga ngg                                           23

<210> SEQ ID NO 7
<211> LENGTH: 23
<212> TYPE: DNA
<213> ORGANISM: Artificial Sequence -continued

```
<220> FEATURE:
<223> OTHER INFORMATION: Synthetic
<220> FEATURE:
<221> NAME/KEY: misc_feature
<222> LOCATION: (21)..(21)
<223> OTHER INFORMATION: n is a, c, g, or t

<400> SEQUENCE: 7
atctaaactg taacattgaa ngg                                           23
```

INTEGRATION SITES AND USES THEREOF

CROSS-REFERENCE TO RELATED APPLICATIONS

This application claims priority to U.S. provisional patent application No. 62/473,454, filed Mar. 19, 2017, the disclosure of which is incorporated herein by reference.

FIELD OF THE INVENTION

The present invention generally relates to compositions and methods for enhanced expression of proteins in eukaryotic cells.

BACKGROUND

Manufacture of recombinant proteins in mammalian cells is of great importance for research or therapeutic uses. The generation of mammalian cell lines with high level and stable expression of the recombinant proteins is the key step in the manufacture process. The most commonly approach of generating such a mammalian cell line involves the steps of 1) transfecting a vector comprising a transgene into mammalian cells such that the transgene may incorporate into the chromosomes of the cells, and 2) selecting cells expressing the transgene at high level. The selection of stably transfected cell lines suitable for the manufacture purposes is often an arduous process, as the maintenance of expression is highly dependent upon the nature of the genomic environment at the site of transgene integration, where epigenetic mechanisms result in variable expression and silencing in the vast majority of cases. Accordingly, there is a continuing need in the art for improved mammalian expression systems.

SUMMARY OF INVENTION

In one aspect, the present disclosure provides a mammalian cell comprising an exogenous nucleic acid sequence integrated within a locus of the genome of the cell, wherein the locus comprises an extended methylation-free CpG island. In one embodiment, the locus is the genomic region selected from the group consisting of the promoter and surrounding region of heterogeneous nuclear ribonucleoprotein A2 (hnRNPA2), the promoter and surrounding region of TATA binding protein (TBP), the CpG island/promoter and surrounding region of beta-actin and the CpG island/promoter and surrounding region of PDCD2. In one embodiment, the locus comprises a nucleotide sequence that is at least 90% identical to SEQ ID NO:1, corresponding to the hnRNPA2 CpG island/promoter locus in Chinese hamster genome. In one embodiment, the locus comprises a nucleotide sequence that is at least 90% identical to SEQ ID NO:2, corresponding to the hnRNPA2 CpG island/promoter locus in human genome. In one embodiment, the locus comprises a nucleotide sequence that is at least 90% identical to SEQ ID NO:3, corresponding to the hnRNPA2 CpG island/promoter locus in mouse genome.

In one embodiment, the cell is a mammalian cell. In one embodiment, the cell is CHO cell. In one embodiment, the cell is an ES cell or a zygote.

In one embodiment, the exogenous nucleic acid sequence comprises an exogenous gene of interest (GOI). In one embodiment, the exogenous nucleic acid sequence comprises an exogenous promoter. In one embodiment, the exogenous nucleic acid encodes a protein. In one embodiment, the exogenous nucleic acid encodes an antibody. In one embodiment, the exogenous nucleic acid sequence comprises one or more recombinase recognition sequences. In one embodiment, the recombinase recognition sequence is selected from the group consisting of an attP site, an attB, a LoxP site, a Lox511 site, a Lox2272 site, a Lox2372 site, a Lox5171 site, a Loxm2 site, a Lox71 site, a Lox66 site, a LoxFas site, a frt site, a site recognized by phiC31 integrase, a site recognized by Bxb1 integrase and a site recognized by Tn3 integrase.

In another aspect, the present disclosure provides a method comprising: introducing into a mammalian cell an exogenous nucleic acid, wherein the exogenous nucleic acid integrates into a locus of the genome, the locus comprising an extended methylation-free CpG island. In one embodiment, the method further comprises developing the cell into an organism.

In yet another aspect, the present disclosure provides a method comprising: (a) providing a cell comprising an exogenous nucleic acid sequence integrated within a locus of the genome of the cell, wherein the exogenous nucleic acid sequence comprises an exogenous GOI operably linked to an exogenous promoter, and wherein the locus comprises an extended methylation-free CpG island; and (b) culturing the cell of (a) under conditions that allow expression of the exogenous GOI. In one embodiment, the exogenous GOI encodes a protein of interest (POI), and the method further comprises recovering the POI.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

DETAILED DESCRIPTION OF THE INVENTION

Figure 1:
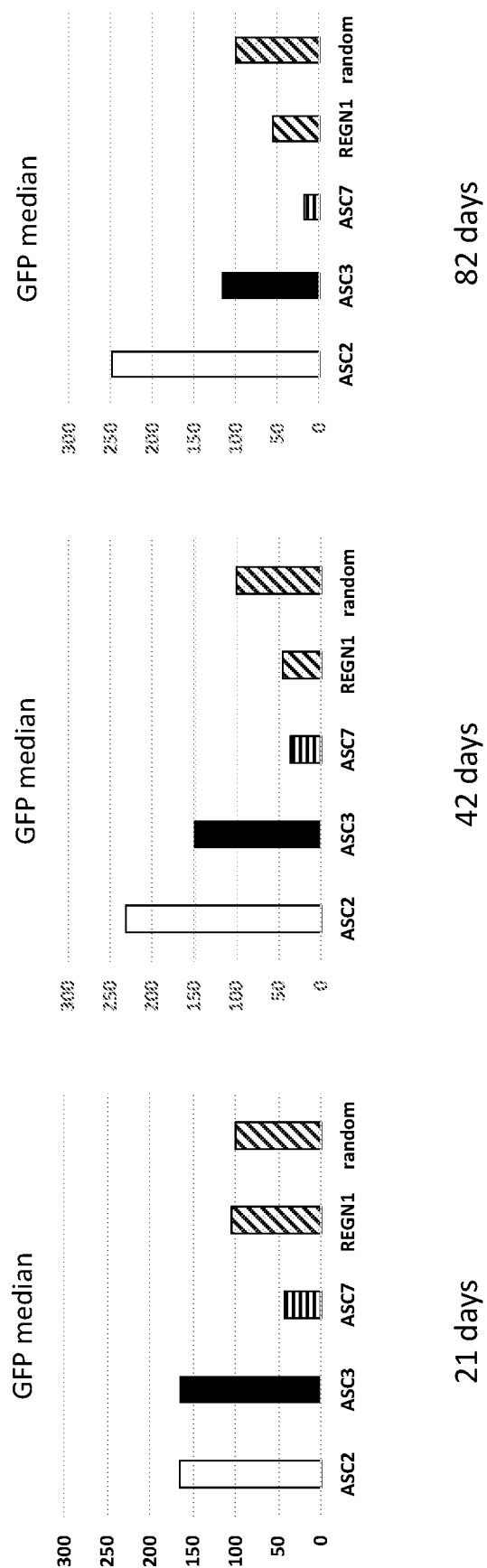
FIG. 1 shows the expression level of GFP when a transgene encoding the GFP was inserted in different loci of CHO cells.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Definitions

The following definitions are provided to assist the reader. Unless otherwise defined, all terms of art, notations and other scientific or medical terms or terminology used herein are intended to have the meanings commonly understood by those of skill in the chemical and medical arts. In some cases, terms with commonly understood meanings are defined herein for clarity and/or for ready reference, and the inclusion of such definitions herein should not necessarily be construed to represent a substantial difference over the definition of the term as generally understood in the art.

As used herein, the singular forms "a", "an" and "the" include plural references unless the context clearly dictates otherwise.

It is noted that in this disclosure, terms such as "comprises", "comprised", "comprising", "contains", "containing" and the like have the meaning attributed in United States Patent law; they are inclusive or open-ended and do not exclude additional, un-recited elements or method steps. Terms such as "consisting essentially of" and "consists essentially of" have the meaning attributed in United States Patent law; they allow for the inclusion of additional ingredients or steps that do not materially affect the basic and novel characteristics of the claimed invention. The terms "consists of" and "consisting of" have the meaning ascribed to them in United States Patent law; namely that these terms are close ended.

The term "antibody" as used herein includes any immunoglobulin, monoclonal antibody, polyclonal antibody, multispecific antibody, or bispecific (bivalent) antibody that binds to a specific antigen or antigens. A native intact antibody comprises two heavy chains and two light chains. Each heavy chain consists of a variable region and a first, second, and third constant region, while each light chain consists of a variable region and a constant region. Mammalian heavy chains are classified as α, δ, ε, γ, and μ, and mammalian light chains are classified as λ, or κ. The antibody has a "Y" shape, with the stem of the Y consisting of the second and third constant regions of two heavy chains bound together via disulfide bonding. Each arm of the Y includes the variable region and first constant region of a single heavy chain bound to the variable and constant regions of a single light chain. The variable regions of the light and heavy chains are responsible for antigen binding. The variable regions in both chains generally contain three highly variable loops called the complementarity determining regions (CDRs) (light (L) chain CDRs including LCDR1, LCDR2, and LCDR3, heavy (H) chain CDRs including HCDR1, HCDR2, HCDR3). CDR boundaries for the antibodies and antigen-binding fragments disclosed herein may be defined or identified by the conventions of Kabat, Chothia, or Al-Lazikani (Al-Lazikani, B., Chothia, C., Lesk, A. M., J Mol Biol 273(4):927 (1997); Chothia, C. et al., J Mol Biol 186(3):651-63 (1985); Chothia, C. and Lesk, A. M., J Mol Biol, 196:901 (1987); Chothia, C. et al., Nature 342 (6252):877-83 (1989); Kabat E. A. et al., National Institutes of Health, Bethesda, Md. (1991)). The three CDRs are interposed between flanking stretches known as framework regions (FRs), which are more highly conserved than the CDRs and form a scaffold to support the hypervariable loops. The constant regions of the heavy and light chains are not involved in antigen binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of α, δ, ε, γ, and μ heavy chains, respectively. Several of the major antibody classes are divided into subclasses such as IgG1 (γ1 heavy chain), IgG2 (γ2 heavy chain), IgG3 (γ3 heavy chain), IgG4 (γ4 heavy chain), IgA1 (α1 heavy chain), or IgA2 (α2 heavy chain).

A "cell", as used herein, can be prokaryotic or eukaryotic. A prokaryotic cell includes, for example, bacteria. A eukaryotic cell includes, for example, a fungus, a plant cell, and an animal cell. The types of an animal cell (e.g., a mammalian cell or a human cell) includes, for example, a cell from circulatory/immune system or organ (e.g., a B cell, a T cell (cytotoxic T cell, natural killer T cell, regulatory T cell, T helper cell), a natural killer cell, a granulocyte (e.g., basophil granulocyte, an eosinophil granulocyte, a neutrophil granulocyte and a hypersegmented neutrophil), a monocyte or macrophage, a red blood cell (e.g., reticulocyte), a mast cell, a thrombocyte or megakaryocyte, and a dendritic cell); a cell from an endocrine system or organ (e.g., a thyroid cell (e.g., thyroid epithelial cell, parafollicular cell), a parathyroid cell (e.g., parathyroid chief cell, oxyphil cell), an adrenal cell (e.g., chromaffin cell), and a pineal cell (e.g., pinealocyte)); a cell from a nervous system or organ (e.g., a glioblast (e.g., astrocyte and oligodendrocyte), a microglia, a magnocellular neurosecretory cell, a stellate cell, a boettcher cell, and a pituitary cell (e.g., gonadotrope, corticotrope, thyrotrope, somatotrope, and lactotroph)); a cell from a respiratory system or organ (e.g., a pneumocyte (a type I pneumocyte and a type II pneumocyte), a clara cell, a goblet cell, an alveolar macrophage); a cell from circular system or organ (e.g., myocardiocyte and pericyte); a cell from digestive system or organ (e.g., a gastric chief cell, a parietal cell, a goblet cell, a paneth cell, a G cell, a D cell, an ECL cell, an I cell, a K cell, an S cell, an enteroendocrine cell, an enterochromaffin cell, an APUD cell, a liver cell (e.g., a hepatocyte and Kupffer cell)); a cell from integumentary system or organ (e.g., a bone cell (e.g., an osteoblast, an osteocyte, and an osteoclast), a teeth cell (e.g., a cementoblast, and an ameloblast), a cartilage cell (e.g., a chondroblast and a chondrocyte), a skin/hair cell (e.g., a trichocyte, a keratinocyte, and a melanocyte (Nevus cell)), a muscle cell (e.g., myocyte), an adipocyte, a fibroblast, and a tendon cell), a cell from urinary system or organ (e.g., a podocyte, a juxtaglomerular cell, an intraglomerular mesangial cell, an extraglomerular mesangial cell, a kidney proximal tubule brush border cell, and a macula densa cell), and a cell from reproductive system or organ (e.g., a spermatozoon, a Sertoli cell, a leydig cell, an ovum, an oocyte). A cell can be normal, healthy cell; or a diseased or unhealthy cell (e.g., a cancer cell). A cell further includes a mammalian zygote or a stem cell which include an embryonic stem cell, a fetal stem cell, an induced pluripotent stem cell, and an adult stem cell.

A stem cell is a cell that is capable of undergoing cycles of cell division while maintaining an undifferentiated state and differentiating into specialized cell types. A stem cell can be an omnipotent stem cell, a pluripotent stem cell, a multipotent stem cell, an oligopotent stem cell and a unipotent stem cell, any of which may be induced from a somatic cell. A stem cell may also include a cancer stem cell. A mammalian cell can be a rodent cell, e.g., a mouse, rat, hamster cell. A mammalian cell can be a lagomorpha cell, e.g., a rabbit cell. A mammalian cell can also be a primate cell, e.g., a human cell. In certain examples, the cells are those used for mass bioproduction, e.g., CHO cells.

A "homologous sequence" in the context of nucleic acid sequences refers to a sequence that is substantially homologous to a reference nucleic acid sequence. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding nucleotides are identical over a relevant stretch of residues. In some embodiments, the relevant stretch is a complete (i.e., full) sequence.

The term "operably linked" refers to an arrangement of elements wherein the components so described are configured so as to perform their usual function. Thus, a given signal peptide that is operably linked to a polypeptide directs the secretion of the polypeptide from a cell. In the case of a promoter, a promoter that is operably linked to a coding sequence will direct the expression of the coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

The term "nucleic acid" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, shRNA, single-stranded short or long RNAs, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

"Percent identity," when describing a nucleic acid sequence, such as SEQ ID NO:1, or a fragment thereof, is meant to include homologous sequences that display the recited identity along regions of contiguous homology, but the presence of gaps, deletions, or insertions that have no homolog in the compared sequence are not taken into account in calculating percent identity. As used herein, a percent identity determination between, e.g., SEQ ID NO:1, or fragment thereof, with a species homolog would not include a comparison of sequences where the species homolog has no homologous sequence to compare in an alignment (i.e., SEQ ID NO:1 or the fragment thereof has an insertion at that point, or the species homolog has a gap or deletion, as the case may be). Thus, "percent identity" does not include penalties for gaps, deletions, and insertions.

The term "promoter" when used in genetics refers to a region of DNA that initiates transcription of a particular gene. Promoters are usually located upstream of the transcription start sites of genes, and can be about 100-1000 base pairs long.

In general, a "protein" is a polypeptide (i.e., a string of at least two amino acids linked to one another by peptide bonds). Proteins may include moieties other than amino acids (e.g., may be glycoproteins) and/or may be otherwise processed or modified. Those of ordinary skill in the art will appreciate that a "protein" can be a complete polypeptide chain as produced by a cell (with or without a signal sequence), or can be a functional portion thereof. Those of ordinary skill will further appreciate that a protein can sometimes include more than one polypeptide chain, for example linked by one or more disulfide bonds or associated by other means.

As used herein, the term "subject" refers to a human or any non-human animal (e.g., mouse, rat, rabbit, dog, cat, cattle, swine, sheep, goat, horse or primate). A human includes pre and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

The term "vector" as used herein refers to a vehicle into which a polynucleotide encoding a protein may be operably inserted so as to bring about the expression of that protein. A vector may be used to transform, transduce, or transfect a host cell so as to bring about expression of the genetic element it carries within the host cell. Examples of vectors include plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Categories of animal viruses used as vectors include retrovirus (including lentivirus), adenovirus, adeno-associated virus, herpesvirus (e.g., herpes simplex virus), poxvirus, baculovirus, papillomavirus, and papovavirus (e.g., SV40). A vector may contain a variety of elements for controlling expression, including promoter sequences, transcription initiation sequences, enhancer sequences, selectable elements, and reporter genes. In addition, the vector may contain an origin of replication. A vector may also include materials to aid in its entry into the cell, including but not limited to a viral particle, a liposome, or a protein coating.

Cells and Organisms with Enhanced Expression of Exogenous Genes

In one aspect, the present disclosure provides a mammalian cell with enhanced expression of exogenous genes. In one embodiment, the cell comprises an exogenous nucleic acid sequence integrated within a locus of the genome of the cell, wherein the locus comprises an extended methylation-free CpG island.

In mammalian DNA, the dinucleotide CpG is recognized by a DNA methyltransferase enzyme that methylates cytosine to 5-methylcytosine. 5-methylcytosine is unstable and is prone to be converted to thymine. As a result, CpG dinucleotides occur far less frequently than one would expect by chance. Some sections of genomic DNA nevertheless have a frequency of CpG that is closer to that is expected by chance, and theses sequences are known as CpG islands. As used herein, a "CpG island" refers to a sequence of DNA, of at least 200 bp, that has a GC content at least 50% and an observed/expected CpG content ratio of at least 0.6 (i.e., a CpG dinucleotide content of at least 60% of which would be expected by chance) (Gardiner-Green M and Frommer M. *J Mol Biol* (1987)196, 261-282; Rice P, Longden I and Bleasby A *Trends Genet* (2000)16, 276-277).

Methylation-free CpG islands are well-known in the art (Bird et al., *Cell* (1985) 40: 91-99; Tazi & Bird, *Cell* (1990) 60: 909-920) and may be defined as CpG islands where a substantial proportion of the cytosine residues are not methylated and which usually extend over the 5' ends of two closely spaced (0.1-3 kb) divergently transcribed genes. These regions of DNA are reported to remain hypomethylated in all tissues throughout development (Wise and Pravtcheva, *Genomics* (1999) 60: 258-271). They are often associated with the 5' ends of ubiquitously expressed genes, as well as an estimated 40% of genes showing a tissue-restricted expression profile (Antequera, F. & Bird, A. *Proc. Natl. Acad. Sci. USA* (1993) 90, 1195-11999; Cross, S. H. & Bird, A. P. *Curr. Opin, Genet. Dev.* (1995) 5, 309-314), and are known to be localized regions of active chromatin (Tazi, J. & Bird, A. *Cell* (1990) 60, 909-920).

An "extended methylation-free CpG island" is a methylation-free CpG island that extends across a region encompassing more than one transcriptional start site and/or extends for more than 300 bp and preferably more than 500 bp. The borders of the extended methylation-free CpG island are functionally defined through the use of PCR over the region in combination with restriction endonuclease enzymes whose ability to digest (cut) DNA at their recognition sequence is sensitive to the methylation status of any CpG residues that are present. One such enzyme is HpaII, which recognizes and digests at the site CCGG, which is commonly found within CpG islands, but only if the central CG residues are not methylated. Therefore, PCR conducted with HpaII-digested DNA and over a region harboring HpaII sites, does not give an amplification product due to HpaII digestion if the DNA is unmethylated. The PCR will only give an amplified product if the DNA is methylated. Therefore, beyond the methylation-free region HpaII will not digest the DNA and a PCR amplified product will be observed, thereby defining the boundaries of the "extended methylation-free CpG island."

In one embodiment, the locus comprising an extended methylation-free CpG island is the genomic region selected from the group consisting of the promoter and surrounding region of heterogeneous nuclear ribonucleoprotein A2 (hnRNPA2), the promoter and surrounding region of TATA binding protein (TBP), the CpG island/promoter and surrounding region of beta-actin and the CpG island/promoter and surrounding region of PDCD2. In one embodiment, the locus disclosed herein comprises a nucleotide sequence that is at least 90% identical to SEQ ID NO:1. In one embodiment, the locus comprises a nucleotide sequence that is at least 90% identical to SEQ ID NO:2. In one embodiment, the locus comprises a nucleotide sequence that is at least 90% identical to SEQ ID NO:3.

The term "enhanced" when used to describe enhanced expression includes an enhancement of at least about 1.2-fold to at least about 5 -fold enhancement in expression over what is typically observed by random integration of an exogenous nucleic acid sequence into a genome or by integration at a different locus, for example, as compared to a pool of random integrants of a single copy of the same expression construct. Fold-expression enhancement observed employing the sequences of the invention is in comparison to an expression level of the same gene, measured under substantially the same conditions, in the absence of an integration to the locus of the invention, for example in comparison to integration at another locus into the same species genome.

When the phrase "exogenous nucleic acid," "exogenous nucleic acid sequence," "exogenous gene" or "exogenous promoter" is used with reference to a locus of interest, the phrase refers to any DNA sequence or gene not present within the locus of interest as the locus is found in nature. For example, an "exogenous nucleic acid sequence" within a CHO locus (e.g., a locus comprising a sequence of SEQ ID NO: 1), can be a hamster gene not found within the particular CHO locus in nature (i.e., a hamster gene from another locus in the hamster genome), a gene from any other species (e.g., a human gene), a chimeric gene (e.g., human/mouse gene), or any other gene not found in nature to exist within the CHO locus of interest.

In certain embodiments, the exogenous gene disclosed herein encodes a protein of interest. Any protein of interest suitable for expression in eukaryotic cells can be used. For example, the protein of interest includes, but is not limited to, an antibody or antigen-binding fragment thereof, a chimeric antibody or antigen-binding fragment thereof, an ScFv or fragment thereof, an Fc-fusion protein or fragment thereof, a growth factor or a fragment thereof, a cytokine or a fragment thereof, or an extracellular domain of a cell surface receptor or a fragment thereof. Proteins of interest may be simple polypeptides consisting of a single subunit, or complex multi-subunit proteins comprising two or more subunits.

In one embodiment, the exogenous nucleic acid sequences disclosed herein comprises an exogenous promoter that is operably linked to an exogenous gene. The exogenous promoter includes, but are not limited to commonly used promoters and enhancers that are derived from viruses such as polyoma, adenovirus 2, simian virus 40 (SV40), and human cytomegalovirus (CMV). Viral genomic promoters, control and/or signal sequences may be utilized to drive expression, provided such control sequences are compatible with the host cell chosen. Non-viral cellular promoters can also be used (e.g., the β-globin and the EF-1α promoters), depending on the cell type in which the exogenous gene is to be expressed.

The exogenous nucleic acid sequence can integrate to the specific locus in the genome through any methods known in the art. In certain embodiments, the exogenous nucleic acid sequence integrates to the specific locus via homologous recombination. For homologous recombination, homologous polynucleotide molecules (i.e., homologous arms) line up and exchange a stretch of their sequence. A transgene can be introduced during this exchange if the transgene is flanked by homologous genomic sequences. In one example, a recombination site can be introduced into the host cell genome at the integration sites.

Homologous recombination in eukaryotic cells can be facilitated by introducing a break in the chromosomal DNA at the integration site. It has been demonstrated that the frequency of homologous recombination during gene targeting increases if a double-stranded break is introduced within the chromosomal target sequence. Gene targeting vectors are also employed to facilitate homologous recombination. In the absence of a gene targeting for homology directed repair, the cells frequently close the double-stranded break by non-homologous end-joining (NHEJ), which may lead to deletion or insertion of multiple nucleotides at the cleavage site. Should insertions or deletions (InDels) occurs, a small number of nucleotides are either inserted to deleted at random at the site of the break and these InDels may shift or disrupt any open reading frame (ORF) of a gene within the target locus. It is understood that the loci contemplated in the invention, e.g., loci with extended methylation-free CpG island, is usually not a gene coding region. Therefore, no disruption of endogenous gene transcription is envisioned by insertion and/or deletion at this locus. Hence, in certain embodiments, the exogenous nucleic acid sequence integrates to the specific locus via non-homologous end joining (NHEJ) mechanisms.

In certain embodiments, the integration of the exogenous nucleic acid is facilitated by a site-specific nuclease. As used herein, a "nuclease" is an enzyme capable of cleaving the phosphodiester bonds between the nucleotide subunits of nucleic acids. A "site-specific nuclease" refers to a nuclease whose functioning depends on a specific nucleotide sequence. Typically, a site-specific nuclease recognizes and binds to a specific nucleotide sequence and cuts a phosphodiester bond within or in the vicinity of the nucleotide sequence. In certain embodiments, double-strand break is generated by site-specific cleavage using a site-specific nuclease. Examples of site-specific nucleases include, without limitation, zinc finger nucleases (ZFNs), transcriptional activator-like effector nucleases (TALENs) and CRISPR (clustered regularly interspaced short palindromic repeats)-associated (Cas) nucleases.

In certain embodiments, the exogenous nucleic acid sequences integrated to the locus comprises a recombinase recognition sequence. As used herein, a recombinase recognition sequence refers to a sequence recognized by a site-specific recombinase. The term "recombinase" or "site-specific recombinase" refers to a family of highly specialized enzymes that promote DNA rearrangement between specific target sites (Greindley et al., 2006; Esposito, D., and Scocca, J. J. *Nucleic Acids Research* (1997) 25, 3605-3614; Nunes-Duby, S. E., et al. *Nucleic Acids Research* (1998) 26, 391-406; Stark, W. M., et al. *Trends in Genetics* (1992) 8, 432-439). Virtually all site-specific recombinases can be categorized within one of two structurally and mechanistically distinct groups: the tyrosine (e.g., Cre, Flp, and the lambda integrase) or serine (e.g., phiC31 integrase, gamma-delta resolvase, Tn3 resolvase and Gin invertase) recombinases. Both recombinase families recognize target sites composed of two inversely repeated binding elements that flank a spacer sequence where DNA breakage and religation occur. The recombination process requires concomitant binding of two recombinase monomers to each target site: two DNA-bound dimers (a tetramer) then join to form a synaptic complex, leading to crossover and strand exchange. "Hyperactive" forms of Tn3 resolvase containing activating mutations in Tn3 resolvase can catalyze strand exchange at a core site of 28bp without accessory sites, presumably through reconfiguration of the tertiary/quaternary structure of the tetramer. In certain embodiments, the recombinase recognition sequence is selected from the group consisting of an attP site, an attB, a LoxP site, a Lox511 site, a Lox2272 site, a Lox2372 site, a Lox5171 site, a Loxm2 site, a Lox71 site, a Lox66 site, a LoxFas site, a frt site, a site recognized by phiC31 and a site recognized by Tn3.

When a recombinase recognition sequence is integrated into a locus of the genome, it can be used to facilitate integration of other nucleic acid sequences into the locus, e.g., through a recombinase mediated cassette exchange (RMCE) process. In one embodiment, the recombinase recognition sequence is attP or attB, recognized by an integrase (e.g., phi C31 and Tn3). For example, when an attP recognized by phiC31 is integrated into the locus of a cell, a transgene can be integrated to the locus by introducing into the cell a vector comprising the transgene and an attB in the presence of phiC31 integrase.

In one embodiment, the cell disclosed herein is an ES cell or a zygote and can be developed into an organism. Accordingly, the present disclosure in another aspect provides a transgenic animal comprising in its germline an exogenous nucleic acid sequence integrated within a locus of the genome, wherein the locus comprises an extended methylation-free CpG island. The animal can be a mouse, a rat, a rabbit, a dog, a cat, a cattle, a sheep, a goat or a non-human primate.

Methods and Compositions for Enhanced Expression of an Exogenous Gene

In another aspect, the present disclosure provides a method for enhanced expression of an exogenous gene in mammalian cells. In one embodiment, the method comprises introducing into a mammalian cell an exogenous nucleic acid, wherein the exogenous nucleic acid integrates into a locus of the genome, the locus comprising an extended methylation-free CpG island.

The term "introduce" in the context of inserting a nucleic acid sequence into a cell, means "transfection", or 'transformation", or "transduction" and includes reference to the incorporation of a nucleic acid sequence into a eukaryotic or prokaryotic cell wherein the nucleic acid sequence may be present in the cell transiently or may be incorporated into the genome of the cell (e.g., chromosome, plasmid, plastid, or mitochondrial DNA), converted into an autonomous replicon. The nucleic acid of the present disclosure may be introduced into a cell using any method known in the art. Various techniques for transforming animal cells may be employed, including, for example: microinjection, retrovirus mediated gene transfer, electroporation, transfection, nanoparticle mediated gene transfer or the like (see, e.g., Keown et al., Methods in Enzymology 1990, 185:527-537). In one embodiment, the vector is introduced to the cell via a virus (e.g., adeno-associated virus).

After the exogenous nucleic acid sequence is introduced into a cell of interest, it can integrate to the specific locus in the genome of the cell through any methods known in the art. In certain embodiments, the exogenous nucleic acid sequence integrates to the specific locus via homologous recombination. In certain embodiments, the exogenous nucleic acid sequence integrates to the specific locus via non-homologous end joining (NHEJ) mechanisms. In one embodiment, the method disclosed herein further comprises introducing to the cell a site-specific nuclease. In one embodiment, the site-specific nuclease is a Cas nuclease. In one embodiment, the method disclosed herein further comprises introducing to the cell a gRNA complement to a sequence of the locus in which the exogenous nucleic acid is integrated.

In one embodiment, the cell used herein is an ES cell or a zygote, and the method disclosed herein further comprises developing the cell into an organism.

In another aspect, the present disclosure provides compositions for enhanced expression of an exogenous gene in mammalian cells.

The present disclosure in another aspect also provides methods of therapy or treatment comprising administering to a subject a therapeutically effective amount of a vector comprising an exogenous nucleic acid, wherein the exogenous nucleic acid integrates into a locus of the genome of a cell of the subject, the locus comprising an extended methylation-free CpG island "Treating" or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof.

Methods for Manufacturing Recombinant Proteins

In another aspect, the present disclosure provides methods of producing recombinant proteins in mammalian cells. In one embodiment, the method comprises (a) providing a cell comprising an exogenous nucleic acid sequence integrated within a locus of the genome of the cell, wherein the exogenous nucleic acid sequence comprises an exogenous GOI operably linked to an exogenous promoter, and wherein the locus comprises an extended methylation-free CpG island; and (b) culturing the cell of (a) under conditions that allow expression of the exogenous GOI. In certain embodiments, the cell disclosed herein is a CHO cell. In one embodiment, the exogenous GOI encodes a protein of interest (POI), and the method disclosed herein further comprises recovering the POI. In one embodiment, the protein of interest is selected from the group consisting of an immunoglobulin, or fragment thereof, and a receptor, or ligand-binding fragment thereof In certain embodiments, the protein of interest is selected from the group consisting of an antibody light chain, or antigen-binding fragment thereof, and an antibody heavy chain, or antigen-binding fragment thereof.

EXAMPLE

The following example is included to demonstrate preferred embodiments. It should be appreciated by those of skill in the art that the techniques disclosed in the examples that follow represent techniques discovered by the inventors to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

This example illustrates that hnRNPA2 locus is an active site for protein expression. CHO-S cells were transfected with linearized CMV-GFP-T2A-puro donor DNA together with a Cas9-gRNA targeting each of the genomic loci that were being tested including ASC2, ASC3, ASC7, and REGN1. ASC2 corresponds to hnRNPA2 (SEQ ID NO:1). ASC3 and ASC7 correspond to two other unrelated loci in the genome. REGN1 refers to an active site described in US Patent Application Publication No. US2016/0115502 A1. Random refers to random integration with donor DNA only and was used as a base-line control. Four days after transfection, cells were selected with puromycin for three days. The surviving cells were cultured with non-selective medium. Cells were collected at 21, 42 and 82 days post transfection and subject to GFP analysis with flow cytometry. The percentage of median value of GFP signals over that of random insertion was plotted (FIG. 1). GFP signal remained more robust for an extended culturing period of 82 days for ASC2 locus compared to all the other loci tested. The gRNA sequences used for ASC2, ASC3, ASC7, and REGN1 targeting are listed in the Table below.

TABLE 1 gRNA sequences targeting different loci

| Locus | Sequence | SEQ ID NO |
|---|---|---|
| ASC2 | TGTAAAATACTTAGTATGACNGG | 4 |
| ASC3 | TGACAATGGGACCAGTAGTANGG | 5 |
| ASC7 | ACTCTGATCAGCTATCTTGANGG | 6 |
| REGN1 | ATCTAAACTGTAACATTGAANGG | 7 |

Example 2

Figure 2:
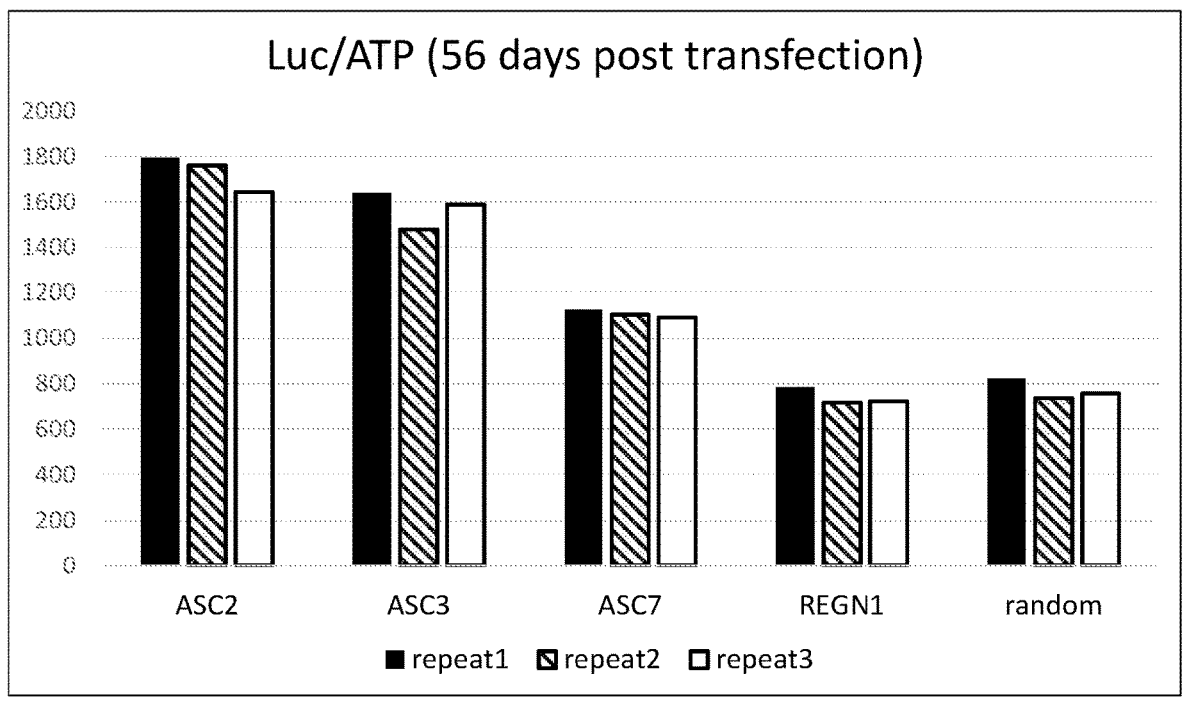
FIG. 2 shows the expression level of luciferase when a transgene encoding the luciferase was inserted in different loci of CHO cells.

This example illustrates that hnRNPA2 locus is an active site for protein expression. CHO-S cells were transfected with linearized CMV-mCherry-PGK-Luc donor DNA together with a Cas9-gRNA targeting each of the genomic loci that were being tested including ASC2, ASC3, ASC7, and REGN1. ASC2 corresponds to hnRNPA2 (SEQ ID NO:1). ASC3 and ASC7 correspond to two other unrelated loci in the genome. REGN1 refers to an active site described in US Patent Application Publication No. US2016/0115502 A1. Random refers to random integration with donor DNA only and was used as a control. Four weeks after transfection, red fluorescent cells expressing mCherry were enriched by FACS and cultured for another four weeks. Luciferase activity were measured with Nano-Glo® Luciferase Assay System (Promega) and normalized by ATP light system (Perkin Elmer). The experiments were done with three individual repeats. Luciferase activity over ATP light signal was plotted (FIG. 2). Sample labelling was the same as in Example 1. Luciferase activity at the ASC2 locus was the highest compared to all the other loci tested.

What is claimed is:

1. A method, comprising:
   introducing an exogenous nucleic acid into an isolated mammalian cell in vitro; and
   integrating the exogenous nucleic acid into a locus of the genome of the isolated mammalian cell using
   (i) a Cas nuclease and a gRNA targeting the locus of the genome, or
   (ii) a recombinase,
   wherein the locus comprising an extended methylation-free CpG island and a nucleotide sequence at least 90% identical to SEQ ID NO:1.

2. The method of claim 1, wherein the isolated mammalian cell is a CHO cell.

3. The method of claim 1, wherein the isolated mammalian cell is an embryonic stem cell or a zygote.

4. The method of claim 1, wherein the exogenous nucleic acid comprises an exogenous gene of interest (GOI).

5. The method of claim 4, further comprising culturing the isolated mammalian cell under conditions that allow expression of the exogenous GOI.

6. The method of claim 5, wherein the exogenous GOI. encodes a protein of interest (POI), and wherein the method further comprises recovering the POI.

7. The method of claim 1, wherein the exogenous nucleic acid comprises a recombinase recognition sequence.

8. The method of claim 7, wherein the recombinase recognition sequence is selected from the group consisting of an attP site, an attB site, a LoxP site, a Lox511 site, a Lox2272 site, a Lox2372 site, a Lox5171 site, a Loxm2 site, a Lox71 site, a Lox66 site, a LoxFas site, a frt site, a site recognized by phiC31 integrase, a site recognized by Bxb1 integrase and a site recognized by Tn3 integrase.

9. The method of claim 1, wherein the exogenous nucleic acid is integrated into the locus of the genome via homologous recombination or non- homologous end joining (NHEJ).

10. The method of claim 1, wherein the locus of the genome comprises a recombinase recognition sequence, and wherein the exogenous nucleic acid is integrated into the locus using a recombinase recognizing the recombinase recognition sequence.

* * * * *